United States Patent [19]

Schneider

[11] Patent Number: 4,955,389
[45] Date of Patent: Sep. 11, 1990

[54] APPARATUS FOR STIMULATION WITH OPTICAL STIMULI

[75] Inventor: Siegfried Schneider, Erlangen, Fed. Rep. of Germany

[73] Assignee: Siemens Aktiengesellschaft, Berlin and Munich

[21] Appl. No.: 223,026

[22] Filed: Jul. 22, 1988

[30] Foreign Application Priority Data

Jul. 27, 1987 [DE] Fed. Rep. of Germany ....... 3724842

[51] Int. Cl.$^5$ .............................................. A61B 5/04
[52] U.S. Cl. ................................... 128/731; 351/243; 128/745
[58] Field of Search .................. 128/731, 745, 897; 351/211, 237, 243

[56] References Cited

U.S. PATENT DOCUMENTS

| | | | |
|---|---|---|---|
| 3,574,450 | 4/1971 | White | 128/731 |
| 3,936,162 | 2/1976 | Krakau et al. | 251/243 |
| 4,094,307 | 6/1978 | Young, Jr. | 128/731 |
| 4,340,274 | 7/1982 | Spooner | 350/128 |
| 4,457,716 | 7/1984 | Eserhaut et al. | 434/20 |

FOREIGN PATENT DOCUMENTS

2096791 10/1982 United Kingdom ................ 351/237

OTHER PUBLICATIONS

Ehnholm et al., "A Seven Channel SQUID Magnetometer for Brain Research" *Physica* 107B, pp. 29–30, 1981.

J. Hohnsbein "Biomagnetismus Signale aus dem Körper" *Bild der Wissenschaft*, No. 8, 1986 pp. 76–83.

Von Ralph Norman Haber "Flugsimulation" *Spektrum der Wissenschaft*, Sep. 1986, pp. 56–64.

Stefan et al. "Biomagnetic Multichannel Measurements in the Pre-Operative Diagnostic Evaluation of Epilepsy" *Electro Medica*, vol. 57 4/89, pp. 129–133.

Stok, *The Inverse Problem in EEG and MEG with Application of Visual Evoked Responses*, Druk:Krips Repro Meppel, 1986, pp. 41–47.

*Primary Examiner*—Randall L. Green
*Assistant Examiner*—Randy Shay
*Attorney, Agent, or Firm*—Hill, Van Santen, Steadman & Simpson

[57] ABSTRACT

The apparatus serves for triggering optically evoked responses in the patient, and the response is acquired by means of a measuring equipment. The apparatus comprises a stimulation signal generator having a surface on which an optical stimulation signal is displayed, a waveguide having a first end and a second end, a first lens system for imaging the signal on the surface into the first end of the waveguide, a second lens system arranged at the second end for imaging the image at the second end onto a presentation surface and a mount for mounting the second lens system and presentation surface a fixed distance from the patient's eyes. In order to reduce possible magnetic interference with the measuring equipment, at least the mount, the second lens system and the waveguide are formed of non-magnetic material.

2 Claims, 1 Drawing Sheet

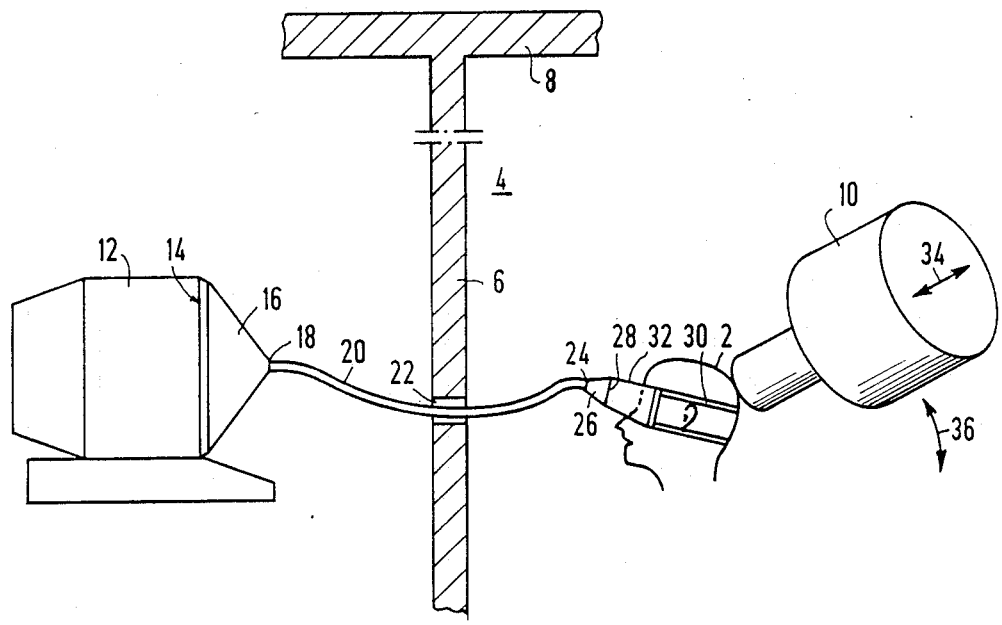

APPARATUS FOR STIMULATION WITH OPTICAL STIMULI

BACKGROUND OF THE INVENTION

The present invention is directed to an apparatus for applying stimulations to a patient comprising an optical stimulation signal generator producing stimulation signals which are supplied to the patient's eye.

The measurement of biomagnetic signals is constantly gaining significance for medical diagnostics, as disclosed by the periodical "Bild der Wissenschaft", No. 8, 1986, pages 76–83. The extremely weak biomagnetic signals can be metrologically acquired with the assistance of a SQUID (superconducting quantum interference device) system, for example a system which can acquire the evoked magnetic fields of the human brain that lie on the order of magnitude of only $10^{-14}$T. The subject is thereby brought into a magnetically shielded measuring space and his head is sensed in a non-contacting fashion with the SQUID system. The data acquired with the assistance of the SQUID technology are then interpreted with the assistance of a computer, based on certain mathematical models.

Magnetic fields induced in the brain by auditory or visual stimuli are of particular interest for experimental research and diagnostics. An apparatus used for the stimulation with optical stimuli must meet certain demands.

It must be taken into consideration that the measurement of optically evoked potentials or magnetic fields at the patient is carried out in a special environment. This can thereby, particularly, involve an electrical or magnetic shielding chamber, the magnetic field of a MR magnet or the proximity of diagnosis and/or therapy equipment, including monitoring and surgical equipment and apparatus working with gas.

It must then be taken into consideration that the measurement is to be carried out with optimally few disturbing influences. Thus, optimally few disturbances should act on the measuring apparatus of the electrical potentials or magnetic fields, for example a SQUID system, on the apparatus for stimulation itself or on the diagnostics equipment, for example an MR recording unit, and on the therapy equipment and, finally, on the subject as well. Relaxation and concentration of the subject are precisely what is necessary for a good signal quality.

Insofar as possible, finally, the measurement should also be capable of being carried out with an optimally great variety of scope or scope of variations in the stimulation in order to also be able to test higher brain functions of the subject.

Optical evokation has heretofore been primarily carried out based on two principles. The first principle is that the subject was shown a checkerboard pattern, for example a field of light and dark portions that are generated with an apparatus similar to a slide projector, with a specifically driven television monitor, or by means of a LED matrix. This checkerboard pattern was directly observed by the subject. Disturbing influences could not be suppressed due to the proximity of the equipment generating the checkerboard pattern.

The second principle is that the eye of the subject was exposed to light flashes that were produced with a flash bulb. This involved a rough function test of the optical signal processing in the brain. Collaboration on the part of the patient, particularly by focusing on a definite spot, was not necessary. Given this principle, eyeglasses could also be used, whereby the light flashes were generated directly in front of the eyes.

In another field, namely that of flight simulation for training pilots, it is known per se to integrate a projection surface into the pilot's helmet. The image presented to the pilot is generated by projectors behind the pilot and is transmitted through fiberglass lenses onto the screen in the helmet, as disclosed in an article from "Spektrum der Wissenschaft", September 1986, pages 56–64, particularly FIG. 3 on page 59.

SUMMARY OF THE INVENTION

The object of the present invention is to provide an apparatus for applying stimulations of optical stimuli to a patient, which includes an optical stimulation signal generator, whose stimulation signals can be supplied to the patient's eye. This apparatus can be utilized in the measurement of optically evoked potentials or magnetic fields of the patient in a special environment, for example a shielded chamber, in a magnetic field of an MR magnet or in a proximity of a diagnostics and/or therapy equipment, and this apparatus leads to optimally few disturbances in the measurement.

This object is inventively achieved in an improvement to the above-mentioned device, which improvement includes a stimulation signal generator comprising a surface on which stimulated signals can be optically displayed, a light waveguide having a first end and a second end, a first lens system that images the stimulated signals of the surface onto the first end of the light waveguide, a second lens system that images the signals transmitted through the waveguide to the second end onto a display surface, said second lens system and display surface being secured to a mount that can be attached to the head of the patient with the patient's eyes looking at the display surface, and that at least the mount, second lens system and light waveguide are constructed of non-magnetic materials.

In accordance with the preferred embodiment, a color graphics station is provided as a stimulation signal generator. This will involve a fast computer that generates a colored graphic on a picture screen in the form of a stationary or moving picture with the assistance of a prescribed program. Dependent on the program, the stimulation signal generated can involve a uniform or non-uniform structure, a variable picture or the like.

The following are noted advantages. Given the apparatus, the stimulation signals are generated at a greater distance from the patient, which distance is defined by the length of the light waveguide and at a greater distance from the measuring and/or therapeutic machine. The patient and the equipment are, thus, disturbed to a relatively slight degree. In case the patient is brought into a shielded chamber, only a small passage for the transmission of the optical signals with the light waveguide is required.

When the color graphics station is employed as a stimulation signal generator, then the great number of different and extremely complex stimuli can be generated in the patient, given a high processing speed.

Other advantages and features of the present invention will be readily apparent from the following description of the preferred embodiment, the claims and drawing.

BRIEF DESCRIPTION OF THE DRAWING

The Figure is a schematic illustration of the apparatus of the present invention.

DESCRIPTION OF THE PREFERRED EMBODIMENTS

The principles of the present invention are particularly useful in an apparatus illustrated in the Figure. The patient, whose head is referenced 2, is accommodated in a shielded chamber 4, which only a side wall 6 and a portion of the ceiling 8 are illustrated. A measuring equipment 10, which is shown in perspective, is provided for measuring optically evoked potentials or magnetic fields and is situated in the chamber 4. This equipment 1 can be a conventional SQUID magnetometer of a conventional type.

In the illustration of the apparatus, a stimulation signal generator 12 that has an image plane or surface 14 on which the optical stimulation signals are planarly portrayable is provided. The surface 14 can, thus, also be referred to as an image plane for the image in the form of structures, signals, etc., which are generated by the stimulation signal generator 12. The stimulation signal generator 12 is, preferably, what is referred to as a color graphics station. The color graphics station will be a fast graphic computer in combination with a picture screen which, dependent on the programing, will create stationary or moving images.

As illustrated, a first lens system 16 is positioned in front of the surface 14 and will focus the generated image of the screen 14 onto one end or a first end 18 of a long light waveguide 20. The long light waveguide is flexible and is conducted through an opening 22 in the wall 6 of the shielded chamber 4. The waveguide has a second or other end 24, which is positioned in the chamber 4. A second lens system 26 is arranged at the second end 24 and images the transmitted stimulation signal onto a presentation surface 28 and the image on the presentation surface 28 is of a smaller size than the first image which was supplied on the screen 14. As may be seen, the first lens system 16 is provided for demagnifying or reducing the image, while the second lens system is provided to magnify or expand the image.

The second lens system 26 and presentation surface 28 are positioned relative to the head 2 so that the patient's eyes will view this surface. To accomplish this, the lens system and surface are provided on a mount 30, which is composed of a non-magnetic material A light shaft or light channel 32, which may be formed of non-magnetic shielding material, extends between the surface 28 and the mount 30 to protect the eyes and block any lateral light from entering the patient's eyes. The mount 30 is constructed to preserve the certain distance between the eye of the patient and the presentation surface 28. In addition to providing non-magnetic material to form the light shaft 32, non-magnetic materials are utilized as materials for at least the mount 30, the second lens system 26 and the light waveguide 20 in order to avoid disturbances in the measurement of the biomagnetic signals.

A helmet, as known for motorcyclists or pilots, can be used as the mount 30. Instead of a helmet, a frame similar to eyeglasses can also be used and is illustrated in the Figure. The frame has a band that, for example, is composed of rubber or plastic that can be looped around the head 2. A firm hold at the head occurs overall so that the patient can fully concentrate on the transmitted, optical signal that he sees on the presentation screen 28.

The measuring equipment 10, for example the SQUID magnetometer, is preferably movable relative to the mount 30 on the basis of motional equipment. This is schematically indicated by a double arrow 34 and by a curve double arrow 36. The optically evoked potentials or, respectively, magnetic fields in the inside of the head can be measured in a non-contacting fashion in this manner.

In that the stimulation signal generator 10 is arranged relatively far from the patient and from the measuring equipment 10, as well as from further diagnostics and/or therapy apparatus, the optically stimulated tespouses can be measured disturbance-free in the patient brain. This is because, in the apparatus of the present invention, the stimulation signal generator is arranged outside of a chamber and a stimulated signal is conveyed into the chamber via a lens system 16, the light waveguide 20 to a second lens system 26. Thus, all possible interference created by the equipment or generator 12 is removed from the measuring equipment 10.

Although various minor modifications may be suggested by those versed in the art, it should be understood that I wish to embody within the scope of the patent granted hereon all such modifications as reasonably and properly come within the scope of my contribution to the art.

I claim:

1. In an apparatus for creating an optical stimulation in a patient who is positioned in chamber means for shielding the patient against outer magnetic fields, said chamber means including a SQUID-magnetometer means being mounted for movement relative to the patient for measuring of magnetic fields originating from the patient due to optically invoked potentials, the improvements comprising a glass fiber light waveguide having a first end face and a second end face, said glass fiber waveguide extending through a wall of said chamber means with the second end face being disposed within said chamber means, generator means for creating stimulation signals being arranged outside of the chamber means, said generator means having a first image plane where the stimulation signals are optically projectable, a first lens means being arranged adjacent said plane for projecting the stimulation signals of said image plane onto said first end face of the glass fiber light waveguide, a second image plane, a second lens means being arranged at the second end face of the glass fiber light waveguide within said chamber for transferring the optical stimulation signals received from said second end face onto said second image plane, mounting means for positioning the second end face of the light waveguide, the second lens means and the second image plane on a head of the patient so that the patient can perceive a picture that appears on the second image plane, and any structure disposed in said chamber means including the second lens means, the mounting means, and the light waveguide being composed of a non-magnetic material.

2. An apparatus according to claim 1, wherein the first lens means includes means for reducing the size of an image as it focuses it on the first end face and wherein the second lens means includes means for expanding the image size as it focuses it onto the second image plane.

* * * * *